United States Patent
Reich et al.

[11] Patent Number: 5,456,660
[45] Date of Patent: Oct. 10, 1995

[54] WOUND DRESSING SUPPORT DEVICE

[76] Inventors: Marshall P. Reich, 1550 S. Potomac, Ste. 350, Aurora, Colo. 80012; Barry F. Shesol, 750 Potomac, Ste. 201, Aurora, Colo. 80011

[21] Appl. No.: 151,956

[22] Filed: Nov. 15, 1993

[51] Int. Cl.$^6$ .............................. A61F 13/00; A61F 15/00
[52] U.S. Cl. .................... 602/79; 128/DIG. 15; 602/59
[58] Field of Search ................. 602/53, 58, 59, 602/79, 78, 47, 42, 41, 75; 128/888, DIG. 15

[56] References Cited

U.S. PATENT DOCUMENTS

| | | | |
|---|---|---|---|
| 3,442,270 | 5/1969 | Steinman | 602/79 |
| 3,779,242 | 12/1973 | McCullough | 602/79 |
| 4,732,146 | 3/1988 | Fasline et al. | 602/79 |
| 4,909,243 | 3/1990 | Frank et al. | 602/58 |

FOREIGN PATENT DOCUMENTS

| | | | |
|---|---|---|---|
| 1253704 | 1/1961 | France | 602/58 |
| 2150028 | 11/1983 | United Kingdom | 602/58 |

*Primary Examiner*—Steven A. Bratlie
*Attorney, Agent, or Firm*—Edwin H. Crabtree; Donald W. Maugolis

[57] ABSTRACT

A wound dressing support device for holding a variety of standard gauze pads in place on top of an open wound and for providing for painless access to the wound. The wound dressing support device consists of an elongated elastic unidirectional wrap which includes a window opening therethrough. The unidirectional wrap is adaptable for conforming to various parts of the anatomy of a patient and includes releasable loop and hook fasteners for securing the wrap around the trunk, head, limb, hand and other parts of the anatomy. The window opening may be of different widths, lengths and geometric shapes for application to different sizes and types of wounds. The window opening is accessed above and on top of one or more gauze pads placed on the wound bed. The wound dressing support device includes loops and hooks around the perimeter of the window opening for releasable engagement of a portion of the sides of the gauze pad. When the dressing is released, the used gauze pad can quickly be removed from the wound bed and replaced with a fresh gauze pad. The window in the wrap allows for visual inspection of the gauze pad relative to the nature of wound drainage, the amount of drainage, and when the dressing needs to be changed. The window further allows for improved evaporation of gases and liquids secreted from the wound and through the gauze pad.

12 Claims, 1 Drawing Sheet

U.S. Patent  Oct. 10, 1995  5,456,660
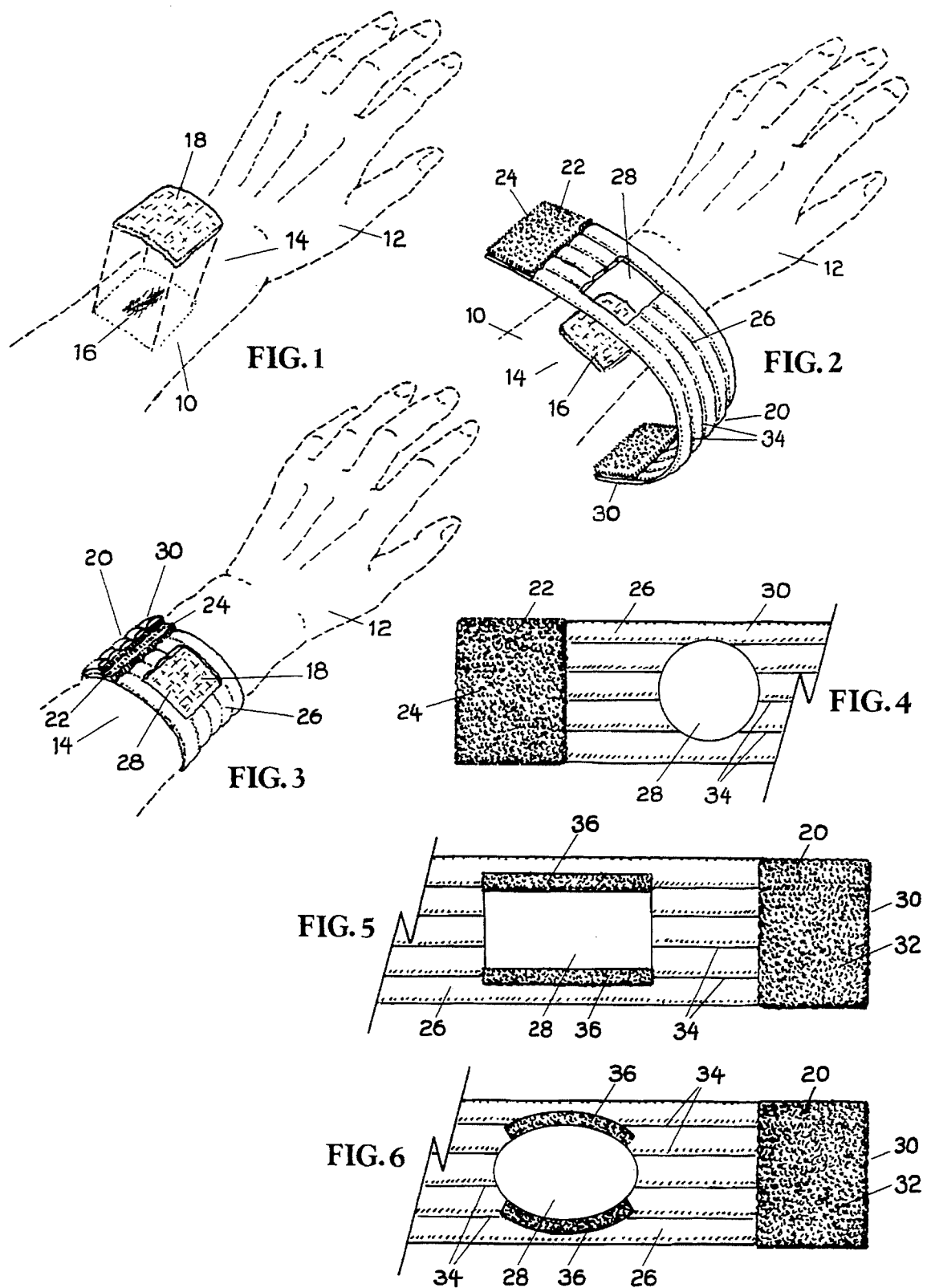

WOUND DRESSING SUPPORT DEVICE

BACKGROUND OF INVENTION (a) Field of the Invention

This invention relates to wound dressings and wound bandages and more particularly, but not by way of limitation, to a wound dressing retaining wrap for holding a gauze pad or the like in place on top of a wound.

(b) Discussion of Prior Art

Because of the complexity of wound healing, the function of a wound dressing may be integral to the success of that process. Wound dressings function as:

a. a protective barrier from outside sources of irritation.

b. provide for mechanical support to the fragile wound surface.

c. serve to form an occlusive barrier to provide an optimal environment for certain wound types.

d. function to absorb wound byproducts that tend to accumulate and complicate healing.

e. act as an agent for wound debridement which acts to clean and prepare a wound bed for healing.

f. may have value as an acceptable camouflage for unsightly wound appearances.

The wound dressing is most often secured in place by the application of an adhesive to the skin. This seemingly simple and universal method of dressing fixation actually has limited applicability accompanied with a significant list of inadequacies, problems and patient dissatisfactions:

a. difficulty with conforming to some anatomic locations and contours, particularly in active body locations.

b. an increasing incidence of adhesive allergies resulting in blister formation, rashes, weeping wounds, scars, and permanent pigmentation problems.

c. inability to adhere in areas of raw, open wounds, or wounds with vulnerable scab formation.

d. lack of satisfactory adherence in hair bearing areas or areas of hypersensitivity.

e. pain associated with adhesive removal in hair bearing areas or areas of hypersensitivity.

f. adhesive system is not reusable when loosened by movement or moisture, thus necessitating reapplication.

g. lack of usefulness in wet to dry dressing situations. Due to the moist dressing, adhesives will not hold the dressings in place, making the wet to dry concept totally ineffective.

h. possibly the most important of issues is that a wound dressing, if not properly chosen, can significantly retard and limit wound healing.

Heretofore there have been a variety of different types of wound dressings using adhesives and stretchable wraps such as described in the following patents.

U.S. Pat. No. 4,732,146 to Fasline et al. discloses a surgical wound dressing device having a frame with an opening for receiving different types of wound dressings. A dressing is held in place by straps attached to one side of the frame with one end of the straps including releasable Velcro fasteners.

U.S. Pat. No. 4,917,112 to Kalt describes a bandage having an opening with the opening covered with a transparent membrane. The membrane is designed to allow air and vapors to permeate outward from the wound and prevent contaminants from entering in the opposite direction.

In U.S. Pat. No. 4,909,243 to Frank et al., a two piece wound dressing is shown having an adhesive layer on one side of a baseplate with an opening in the baseplate to expose the wound and the epithelium area around the wound. A second adhesive layer on one side of a wound pad secures a wound dressing above the opening in the baseplate.

U.S. Pat. Nos. 4,907,579 to Kum, 5,167,613 to Karami et al., and 3,779,242 to McCullough disclosed different types of adhesive bandages for providing open areas to wounds to enhance healing. In U.S. Pat. No. 5,036,838 to Sherman, a foam plastic orthopedic fabric is described having a Velcro tab at one end of the fabric.

In U.S. Pat. No. 4,470,410 to Elliott a stretchable sleeve is shown with Velcro fasteners at the ends of the sleeve. The sleeve includes a central opening with a releasable flap for retaining an intravenous tube or the like.

U.S. Pat. Nos. 4,709,695 to Kohn et al., 4,399,816 to Spangler, 5,086,763 to Hathman, and 4,926,883 to Strock all describe different types of wound surrounding dressings and bandages. Also U.S. Pat. Nos. 4,190,054 to Brennan and 4,658,811 to Beaird disclose stretchable bandages having loop and hook type attachment ends for encircling the head of a patient.

None of these prior art patents disclose the unique structure and advantages of the subject invention as described herein when addressing the need of improved wound debridement and enhanced healing of a wound.

SUMMARY OF THE INVENTION

In view of the foregoing, it is an object of the present invention to provide a wound dressing support device which is easy to apply and holds a variety standard cotton gauze pads in place on top of a wound.

Another object of the invention is to provide a dressing support device that eliminates the need of adhesive tape which causes pain during removal, possible allergic reactions, and flimsy application due to hair, moisture and wound complications.

Still another object of the subject wound dressing support device is the device includes a reusable wrap with a window opening therethrough. The window is accessed over the top of the gauze pad and allows for visual inspection relative to the amount of drainage from the wound and affords an indication on when the gauze pad needs to be changed. The window opening provides a window for the gauze pad or dressing to breathe and allow gases and liquids secreted from the wound to evaporate thereby allowing for improved debridement. Also of importance is that the subject dressing support device is extremely useful in wet to dry dressing applications.

Yet another object of the dressing support device is that the wrap is provided with releasable loop and hook fasteners around the perimeter of the inside of window for securing the gauze pad in place on top of the wound and allowing for quick release of the used pad when applying a fresh dressing to the wound.

A further object of the invention is that the device is lightweight, nonconstricting, versatile and able to be applied by a single individual. Also the wrap is stretchable for ease in conforming to different parts of the anatomy of the trunk, the hand, the head and the limbs.

In summation, the subject invention eliminates the deficiencies of other prior art dressing systems while offering the following objects and advantages that support, simplify, and promote wound healing. They are:

a. reusable, washable, lightweight and non-allergenic dressing system.
b. ease in application and removal by the patient, not requiring, in most instances, the use of more than one hand.
c. adaptable to different anatomic locations and wound sizes.
d. allows visualization of the wound and/or dressing.
e. improves evaporation of gases and fluids from the wound surface to the dressing.
f. promotes reduced pressure to the wound bed by the nature of the dressing window.
g. preserves the integrity of the skin by avoiding adhesives and abrasive materials.
h. allows frequent dressing changes with minimal disruption to the wound bed or local tissues.
i. acts as a brace to support the wound and its surrounding tissues.

The subject wound dressing support device provides for holding a variety of standard gauze pads in place on top of a wound bed for painless access to the wound, increased wound debridement, and enhanced healing. The support dressing consists of an elongated elastic unidirectional wrap with a window opening therethrough. The dressing is adaptable for conforming to various parts of the anatomy of a patient. The window opening may be of different sizes and geometric shapes for receipt of different sizes and types of wounds. The ends of the dressing include releasable loop and hook fasteners for securing the wrap around the trunk, head, hand, limb and other parts of the anatomy. The window opening is accessed above and on top of the gauze pad disposed on top of the wound. The dressing includes loop and hook fasteners around the perimeter of the window opening for releasable engagement of a portion of the side of the gauze pad. When the dressing is released, the used gauze pad can quickly be removed from the top of the wound and replaced with a fresh gauze pad. The dressing is reusable for holding the new gauze pad in place. The window in the wrap allows for visual inspection of the gauze pad relative to the nature of wound drainage, the amount of drainage, and when the dressing needs to be changed. The window further allows for improved evaporation of gases and liquids secreted from the wound and improvements in wet to dry dressing applications.

These and other objects of the present invention will become apparent to those familiar with medical dressings and problems related to the healing of wounds and sores from the following detailed description, showing novel construction, combination, and elements as herein described, and more particularly defined by the appended claims, it being understood that changes in the precise embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a perspective view of a conventional cotton gauze pad received over a wound bed on the top of the forearm.

FIG. 2 is a similar perspective view as shown in FIG. 1 with the window opening of the wound dressing support device received over the gauze pad. The gauze pad on top of the wound.

FIG. 3 is a perspective view as shown in FIGS. 1-2 with the wound dressing support device and gauze pad in place on the wound and the support device secured around the forearm.

FIG. 4 is a top view of a portion of the wound dressing support device with one end having loop fasteners and the window opening being annular in shape.

FIG. 5 is the underside view of a portion of the wound dressing support device with one end having hook fasteners and the window opening being angular in shape with hook fasteners around the perimeter of the opening.

FIG. 6 is the underside view of a portion of the wound dressing support device with one end having hook fasteners and the window opening being annular in shape with hook fasteners around opposite sides of the opening.

DESCRIPTION OF THE PREFERRED EMBODIMENTS

In FIG. 1, a perspective view of a human forearm 10 with hand 12 is shown. In this view a top 14 of the forearm 10 has an open wound 16. A conventional cotton gauze pad 18 is shown above the wound 16 and ready to be lower thereon.

In FIG. 2 the gauze pad 18 has been placed on top of the wound 16 and the subject wound dressing support device having general reference numeral 20 is positioned above the forearm 10. The support device 20 includes a first end 22 having loop fasteners 24 on the top thereof, an elongated elastic unidirectional wrap 26 having a window opening 28 therein, and a second end 30 having hook fasteners 32 on the bottom thereof. In this drawing the window opening 28 is shown disposed above the gauze pad 18. The window opening 28, in this example, is shown angular in shape. It should be kept in mind that the window opening can have various geometric shapes and sizes. Also, the wrap 26 can be of different lengths, sizes, and shapes depending on the type and size of wound and the wound's location on the human anatomy.

Further, while the hook and loop fasteners 32 and 24 are shown there are a variety of other types of releasable securing devices that can be used equally well for securing the opposite ends of the wrap 26 without departing from the spirit and scope of the invention as described herein.

The wrap 26 is unidirectional along it's length for stretching the wrap 26 when it is applied around a portion of the body or limb. The wrap 26 also includes parallel lines 34 of weakness which prevent it from being stretched along it's width and thus distort the window opening 28. It is important for the window opening 28, not only to expose the gauze pad 18, but also to engage the sides of the pad 18 and hold the pad 18 in place on top of the wound 16. Therefore, maintaining the shape and size of the window opening 28, when using the device 20, is of special consideration.

The wrap 26 as described is made by George C. Moore Co. of Westerly, Rhode Island. While this type of wrap is mentioned, other types of elastic wraps of similar construction can also be used with like results.

In FIG. 3 the second end 30 of the wrap 26 has been wrapped around the lower arm 10 and the hook fasteners 32 releasably secured to the loop fasteners 24. The window opening 28 is received on top of the gauze pad 18 with sides of the opening 28 engaging sides of the gauze pad 18 thereby holding the pad 18 in place. While only one pad 18 is shown in the drawings, it can be appreciated that depending on the type of wound and it's characteristics, one or more pads 18 can be placed one on top of each other. As mentioned above, the window opening 28 provides a quick visual means for a doctor or patient to determine when the gauze pad 18 needs to be replaced. Also, because the pad 18 has a loose "loop like" woven structure, the pad 18 with window opening 28 allows the wound 16 to breathe easily thereby allowing a free flow of liquids and gases to escape to the atmosphere for enhanced wound debridement.

In FIG. 4, a top view of a portion of the support device 20 is shown with the first end 22 having the loop fasteners 24 and the wrap 26 having an annular window opening 28. The annular opening 28 can be used with certain types of open wounds needing this type of geometric configuration.

In FIGS. 5–6, a bottom view of a portion of the support device 20 is shown with the second end 30 having the hook fasteners 32 and the wrap 26 having an angular opening 28 in FIG. 5 and an annular opening 28 in FIG. 6. It is important to note in these two drawings that the inside of the window openings 28 is placed hook fastener strips 36.

In operation the fastener strips 36 are used to engage the loose "loop like" weave of the wound cover pad 18 for making sure the pad 18 is held in place on top of the wound 16 when using the subject reusable support device 20. When applying a new pad 18 to the wrap 26 for dressing a wound, opposite sides of the pad 18 are pressed against the fastener strips 36 adjacent the opening 28. The pad 18 is now held in place when received on top of the wound 16. When the pad 18 needs to be replaced, the second end 30 of the wrap 26 is quickly released from the first end 22 and the wrap 26 is unwrapped. Because the device 20 uses no adhesives, hair bearing areas, moist areas and hypersensitive areas of the skin are not bothered during the gauze pad change out.

When the wrap 26 is removed from the wound area, the used pad 18 is released from the fastener strips 36 and a new pad 18 is secured to the strips 36. The device 20 is again reused with the new pad 18 placed carefully over the wound 16. It is important to note that a doctor or patient may prefer the use of a non-adhering dressing, transparent dressing, or other type of wound dressing placed on top of the open wound 16 with the gauze pad 18 placed on top of the other choice of dressing. In this example, the wrap 26 would still be used to engage and hold in place the gauze pad 18. When the dressing is changed, the gauze pad 18 and the dressing on top of the wound 16 would both be changed and the wrap 26 reused with a new sterile dressing and a new gauze pad.

While the invention has been particularly shown, described and illustrated in detail with reference to the preferred embodiments and modifications thereof, it should be understood by those skilled in the art that changes in form and detail may be made therein without departing from spirit and scope of the invention as claimed, except as precluded by the prior art.

The embodiments of the invention for which an exclusive privilege and property right is claimed are defined as follows:

1. A reusable wound dressing support device for holding a gauze pad in place on top of a wound and providing for painless access to the wound, the device adaptable for conforming to various parts of the anatomy of a patient, the device comprising:

an elongated wrap having a top and a bottom, said wrap having a window opening therethrough, said window opening adapted for receipt above and on top of the gauze pad disposed on top of the wound;

a non-adhesive fastener means disposed on the bottom of said wrap and along at least one side of said window opening for releasably engaging a portion of the gauze pad; and securing means attached to opposite ends of said wrap for securing said wrap on the patient.

2. The device as described in claim 1 wherein said window opening is angular in shape and sides of said window opening engaging a portion of sides of the gauze pad.

3. The device as described in claim 1 wherein said window opening is annular in shape and sides of said window opening engaging a portion of sides of the gauze pad.

4. The device as described in claim 1 wherein said fastener means disposed along opposite sides of the window opening for releasably engaging a portion of the sides of the gauze pad.

5. A reusable wound dressing support device for holding one and more gauze pads in place on top of a wound and providing for painless access to the wound, the device adaptable for conforming to various parts of the anatomy of a patient, the device comprising:

an elongated wrap having a top and a bottom, said wrap having a window opening therethrough, said window opening adapted for receipt on top of one of the gauze pads disposed on top of the wound;

a non-adhesive fastener means disposed on the bottom of said wrap and along the sides of said window opening for releasably engaging a portion of one of the gauze pads; and securing means attached to opposite ends of said wrap for securing said wrap on the patient.

6. The device as described in claim 5 wherein said wrap is an elastic unidirectional wrap along a length of said wrap.

7. The device as described in claim 6 wherein said elastic unidirectional wrap includes parallel lines of weakness along the length of said wrap, said parallel lines of weakness preventing a stretching of a width of said wrap and thus distorting a configuration of said window opening.

8. The device as described in claim 5 wherein said securing means is a loop fastener attached to a first end of said wrap and a hook fastener attached to a second end of said wrap.

9. The device as described in claim 5 wherein said fastener means is a hook fastener for releasably engaging a loose "loop like" weave in the gauze pad.

10. A reusable wound dressing support device for holding one and more gauze pads in place on top of a wound and providing for painless access to the wound, the device adaptable for conforming to various parts of the anatomy of a patient and can be applied with one hand, the device comprising:

an elongated elastic unidirectional wrap having a top and a bottom, said wrap having a window opening therethrough, said window opening adapted for receipt on top of the gauze pad disposed on top of the wound, sides of said window opening adapted for engaging sides of the pad;

a non-adhesive fastener means disposed on the bottom of said wrap and along the sides of said window opening for releasably engaging a portion of one of the gauze pads; and securing means attached to opposite ends of said wrap for securing said wrap on the patient.

11. The device as described in claim 20 wherein said securing means is a loop fastener attached to the top of a first end of said wrap and a hook fastener attached to the bottom of a second end of said wrap.

12. The device as described in claim 10 wherein said fastener means is a hook fastener disposed on the bottom of said wrap and on opposite sides of said window opening and along the length of said wrap for releasably engaging a loose "loop like" weave in the gauze pad and holding the pad in place on top of the wound.

* * * * *